(12) United States Patent
Marcelpoil et al.

(10) Patent No.: US 9,547,801 B2
(45) Date of Patent: Jan. 17, 2017

(54) METHODS OF CHROMOGEN SEPARATION-BASED IMAGE ANALYSIS

(71) Applicant: TRIPATH IMAGING, INC., Burlington, NC (US)

(72) Inventors: Raphaël Marcelpoil, Grenoble (FR); Ryan Williams, Carrboro, NC (US); Cédrick Orny, Grenoble (FR)

(73) Assignee: TriPath Imaging, Inc., Burlington, NC (US)

( * ) Notice: Subject to any disclaimer, the term of this patent is extended or adjusted under 35 U.S.C. 154(b) by 625 days.

(21) Appl. No.: 13/946,723

(22) Filed: Jul. 19, 2013

(65) Prior Publication Data

US 2013/0301899 A1 Nov. 14, 2013

Related U.S. Application Data

(62) Division of application No. 11/433,114, filed on May 12, 2006, now Pat. No. 8,492,156.

(60) Provisional application No. 60/680,991, filed on May 13, 2005.

(51) Int. Cl.
| | |
|---|---|
| *G06K 9/34* | (2006.01) |
| *G06K 9/00* | (2006.01) |
| *G01N 1/30* | (2006.01) |
| *G01N 1/31* | (2006.01) |
| *G06T 7/00* | (2006.01) |

(52) U.S. Cl.
CPC ........ *G06K 9/34* (2013.01); *G01N 1/30* (2013.01); *G01N 1/31* (2013.01); *G06K 9/0014* (2013.01); *G06T 7/0012* (2013.01); *G06T 7/0081* (2013.01); *G06T 7/0091* (2013.01); *G06T 2207/10016* (2013.01); *G06T 2207/10056* (2013.01); *G06T 2207/20148* (2013.01); *G06T 2207/20152* (2013.01); *G06T 2207/30024* (2013.01)

(58) Field of Classification Search
CPC .......... G01N 1/30; G01N 1/31; G06K 9/0014; G06K 9/34; G06T 7/0012; G06T 7/0081; G06T 2207/10016; G06T 2207/10056; G06T 2207/20148
USPC .......... 436/63; 382/274, 162, 133; 250/484.5
See application file for complete search history.

(56) References Cited

U.S. PATENT DOCUMENTS

| | | | |
|---|---|---|---|
| 6,134,354 | A | 10/2000 | Lee et al. |
| 6,453,060 | B1 | 9/2002 | Riley et al. |
| 7,065,236 | B2 | 6/2006 | Marcelpoil et al. |
| 7,117,098 | B1 | 10/2006 | Dunlay et al. |

(Continued)

FOREIGN PATENT DOCUMENTS

| | | |
|---|---|---|
| EP | 1065496 | 3/2001 |
| JP | H05-340816 A | 12/1993 |

(Continued)

OTHER PUBLICATIONS

Office Action for Canadian Application No. 2,607,609; dated Oct. 23, 2012.

(Continued)

*Primary Examiner* — Rebecca M Fritchman
(74) *Attorney, Agent, or Firm* — Lerner, David, Littenberg, Krumholz & Mentlik, LLP

(57) ABSTRACT

Methods for chromogen separation-based image analysis are provided, with such methods being directed to quantitative video-microscopy techniques in cellular biology and pathology applications.

2 Claims, 14 Drawing Sheets

(56) References Cited

U.S. PATENT DOCUMENTS

| | | | |
|---|---|---|---|
| 7,989,209 | B2 | 8/2011 | Marcelpoil et al. |
| 2002/0001402 | A1 | 1/2002 | Berliner |
| 2002/0050988 | A1 | 5/2002 | Petrov et al. |
| 2002/0196964 | A1 | 12/2002 | Stone et al. |
| 2003/0091221 | A1 | 5/2003 | Marcelpoil et al. |
| 2003/0138140 | A1 | 7/2003 | Marcelpoil et al. |
| 2005/0254722 | A1* | 11/2005 | Fattal et al. ............ 382/274 |
| 2006/0173266 | A1* | 8/2006 | Pawluczyk et al. ......... 600/407 |
| 2010/0061618 | A1 | 3/2010 | Marcelpoil et al. |
| 2010/0067775 | A1 | 3/2010 | Marcelpoil et al. |

FOREIGN PATENT DOCUMENTS

| | | |
|---|---|---|
| JP | 2005-504276 A | 2/2005 |
| JP | 2005-509140 A | 4/2005 |
| WO | 03025554 A2 | 3/2003 |

OTHER PUBLICATIONS

Office Action for Mexican Application No. MX/a/2007/014016; dated Nov. 27, 2012.
Office Action for U.S. Appl. No. 12/260,701; dated Oct. 26, 2011.
Office Action for U.S. Appl. No. 13/620,670 dated Jan. 4, 2012.
Office Action for U.S. Appl. No. 12/620,670, mailed Aug. 2, 2012.
Office Action for Japanese Application No. 2008-511426 dated Oct. 2, 2012.
Office Action for Korean Application No. 10-2007-7028983 dated Jul. 24, 2012.
Zhou, R., et al., "A Multiple Wavelength Algorithm in Color Image Analysis and its Applications in Stain Decomposition in Microscopy Images," *Medical Physics*, 1996, pp. 1977-1986, vol. 23(12).
Ancin, H., et al., "Advances in Automated 3-D Image Analysis of Cell Populations Imaged by Confocal Microscopy", *Cytometry*, 1996, pp. 221-234, vol. 25, No. 3.
Goesele, M., et al., "Color Calibrated High Dynamic Range Imaging with ICC Profiles", *Proceedings of the 9th IS&T Color Imaging Conference*, Scottsdale, Arizona, Nov. 6, 2001, pp. 286-290.
Madden, B.C., "Extended Intensity Range Imaging", *Tech. Report*, Dec. 17, 1993, University of Pennsylvania, GRASP Laboratory, pp. 1-19.
Malpica, N. et al., "Automated Nuclear Segmentation in Fluorescence Microscopy", *Science, Technology and Education of Microscopy: An Overview*, Jan. 2005, pp. 614-621.
Malpica, N., et al., "Applying Watershed Algorithms to the Segmentation of Clustered Nuclei", *Cytometry*, Nov. 1, 1996, pp. 221-234, vol. 25, No. 3.
Press, W.H. et al., "Numerical Recipes in C", The Art of Scientific Computing, Second Edition, 949 pages.
International Preliminary Examination Report on Patentability for International Application No. PCT/US2006/018516, dated Sep. 27, 2007 (pp. 1-14), including replacement claims (pp. 35-43).

\* cited by examiner

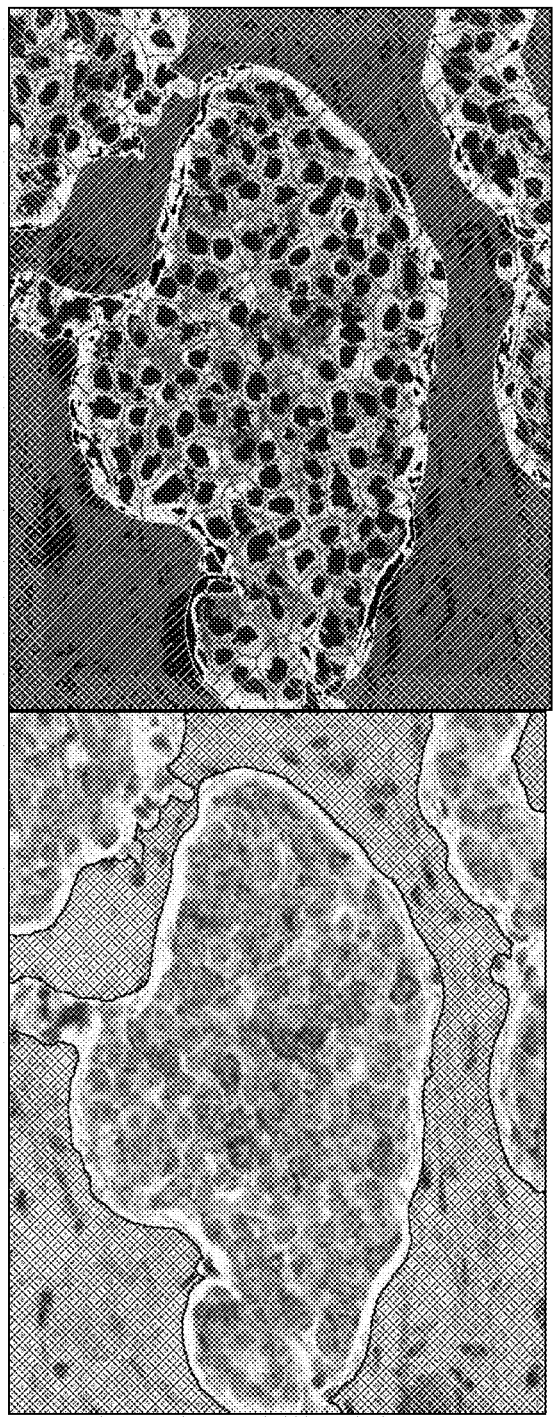
FIG. 3A2
FIG. 3A1

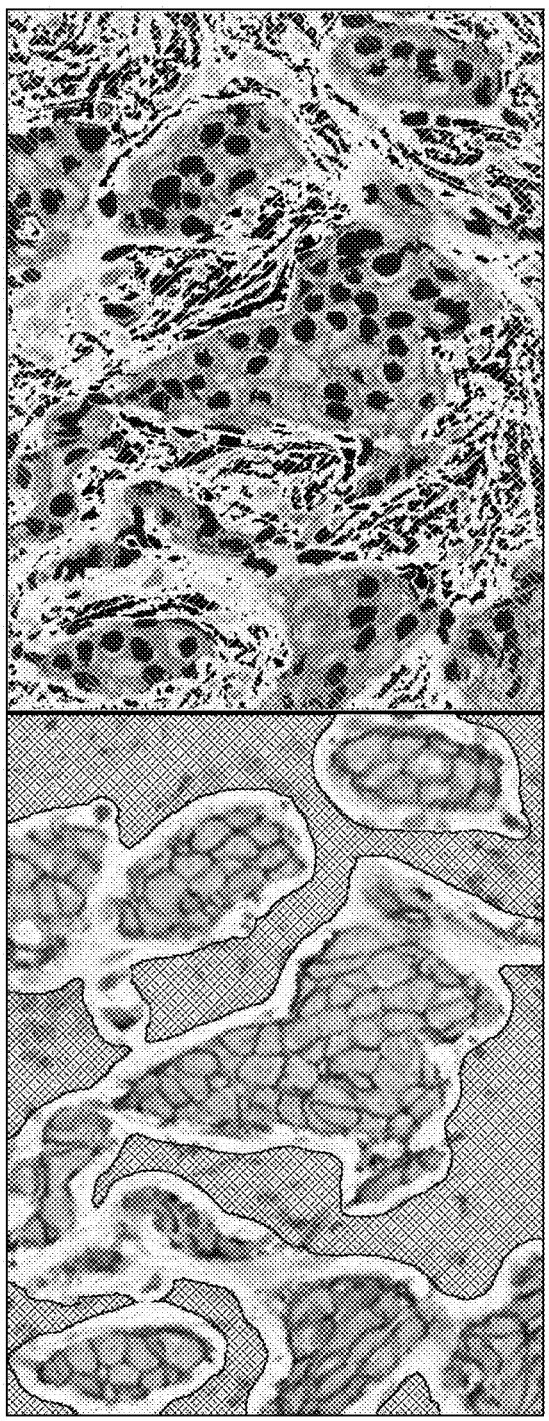
FIG. 3B1
FIG. 3B2

| 1/Integration Time | R | G | B |
|---|---|---|---|
| 4000 | 16 | 7 | 11 |
| 2000 | 39 | 16 | 22 |
| 1000 | 80 | 36 | 53 |
| 500 | 163 | 75 | 114 |
| 250 | 255 | 157 | 237 |
| 100 | 255 | 255 | 255 |

| Integration Time | Odr | Odg | Odb |
|---|---|---|---|
| 0.00025 | 1.20242 | 1.561442 | 1.365147 |
| 0.0005 | 1.116506 | 1.50345 | 1.365147 |
| 0.001 | 1.10551 | 1.452298 | 1.284324 |
| 0.002 | 1.097443 | 1.434569 | 1.252725 |
| 0.004 | 1.097443 | 1.414761 | 1.235912 |
| 0.01 | 1.097443 | 1.414761 | 1.235912 |

FIG. 5B

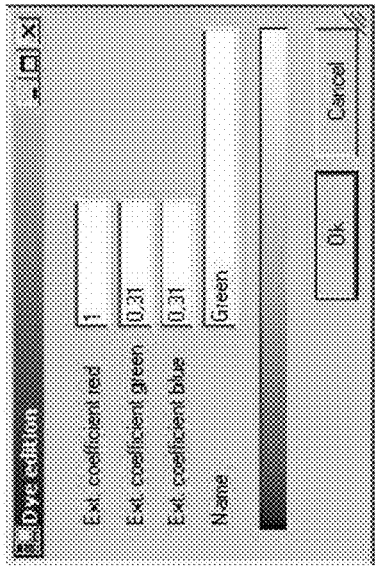
FIG. 6A
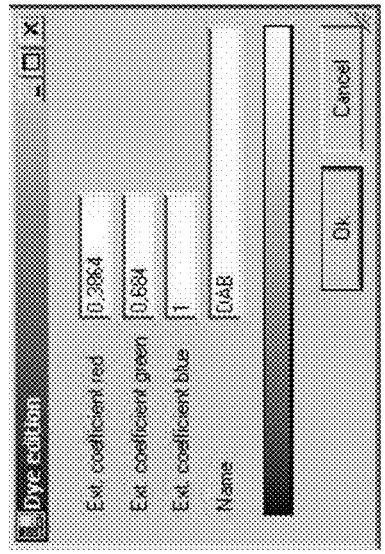
FIG. 6C
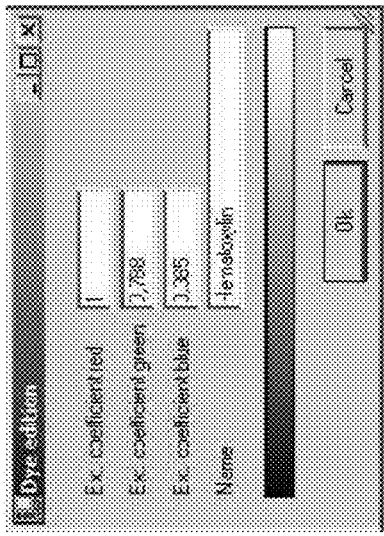
FIG. 6B
FIG. 6D

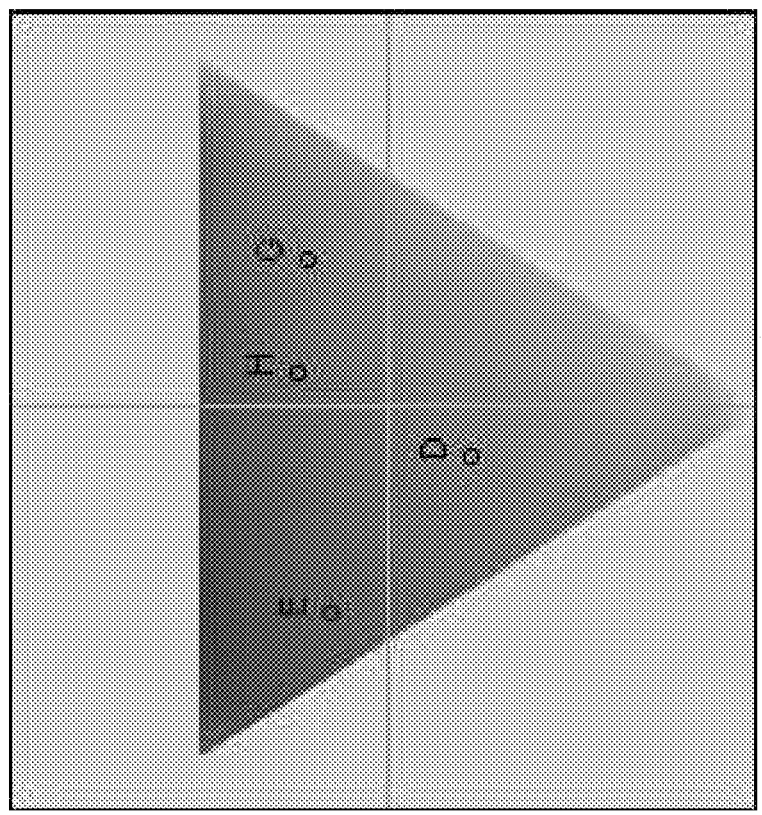

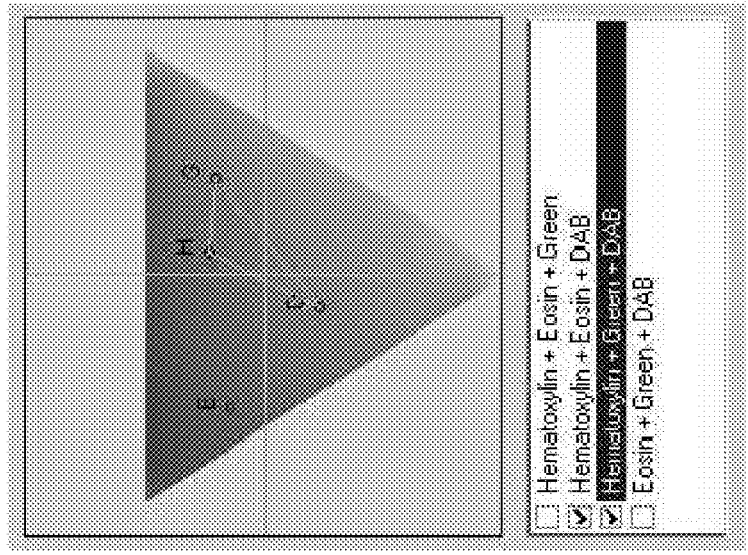
FIG. 7B2
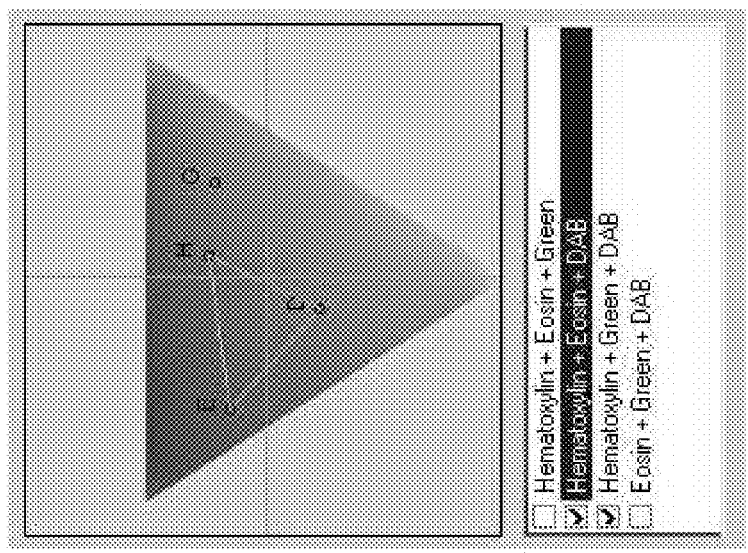
FIG. 7B1

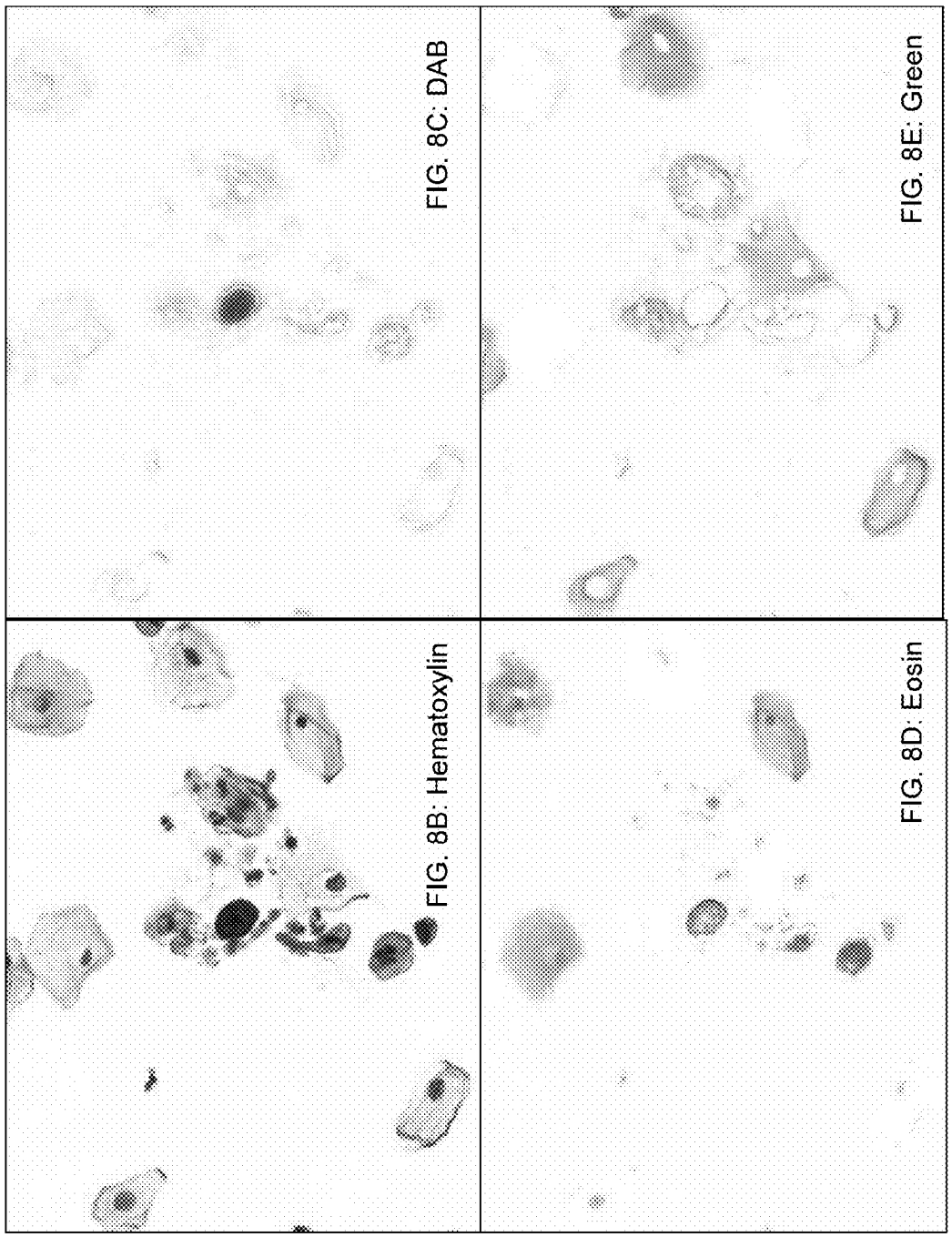

METHODS OF CHROMOGEN SEPARATION-BASED IMAGE ANALYSIS

CROSS-REFERENCE TO RELATED APPLICATIONS

This application is a divisional application of U.S. application Ser. No. 11/433,114, filed May 12, 2006, which claims the benefit of U.S. Provisional Application No. 60/680,991, filed May 13, 2005, each of which is incorporated by reference herein in its entirety.

BACKGROUND OF THE INVENTION

Field of the Invention

The present invention relates to image analysis and, more particularly, to methods for chromogen separation-based image analysis related to quantitative video-microscopy techniques in cellular biology and pathology applications.

Description of Related Art

The assessment and analysis of tissues is the domain of pathology. During the recent past, methodological and technological developments have turned digital image analysis into one of the most efficient tools to assist pathologists in interpreting images with increased accuracy. Though such image analysis techniques contribute substantially to provide cytologists with accurate, reproducible and objective cellular analysis, histological interpretation techniques still tend to depend on the subjective analysis of specimens. Such histological interpretation techniques may also be subject to varying intra- as well as inter-observer agreement, which further tend to provide less accurate, less reproducible, and less objective results. For such reasons, image analysis of tissues was initially restricted to technologies developed for the analysis of cytological specimens.

With the evolution and availability of high performance computers, local and wide area communication, cost-effective database solutions, improved storage technology, and cost-effective high-resolution digital cameras and/or scanners, the situation has now changed. More sophisticated algorithms, formerly ineffective due to lack of CPU power, could not before be applied to tissue sections in a routine environment. However, such algorithms can now be used to assess and quantify tissue-specific features related to marker quantification and sub cellular localization. At the same time, more comprehensive support for a reproducible and more standardized visual assessment of tissue sections has become available based on the initial step in image analysis, namely the creation and management of digital images. This is especially true in the fields of quality control, quality assurance and standardization. Digital images of difficult cases can be exchanged with reference pathologists via telepathology to get a second opinion. Such images can also be effectively used for proficiency testing. Digital images are also the basis of powerful image reference databases, which can be accessed via network, and play an increasingly important role in the documentation of cases and evaluation results, particularly in comprehensive electronic or printed reports.

Once a tissue slide is prepared, a pathologist visually examines the tissue specimen under a microscope. If image analysis should be applied with respect to the slide, the microscope must be at least equipped with a camera or other image capturing device, which is connected to a computer system via an interface. The camera samples the optical microscopic image of the tissue sample via the microscope. As a result, a digital image is collected in the memory of the computer and can be displayed on the monitor thereof. However, the acquisition of these digital images must be performed such that the important details of the optical images are still correctly represented by the stored data.

Generally, the next step for a quantitative assessment of the digitized images is segmentation, which sometimes includes an additional intermediate step of preprocessing. During segmentation, the cells are separated from each other and from the image background. In some instances, algorithmic advances have made it possible to segment cells down to the sub-cellular component level (i.e., nucleus, cytoplasm, and membranes). Although it may appear an easy task, segmentation is often a difficult and error-prone step in image analysis. For slides where the cells are nicely separated and stained in a way that good contrasts occur in the digitized image, segmentation can be done very reliably in many cases. As soon as one of the above conditions is not fulfilled, however, highly sophisticated and time consuming segmentation algorithms, using additional a priori knowledge about the cells and their relationship to each other, or about marker and counter stain sub-cellular localization, have to be applied. This is the case, for example, in instances of tissue sections of infiltrating tumors, where most of the cells are no longer nicely separated on the slide, but tend to be touching and overlapping each other.

Using a marker-based algorithm, it is possible to circumscribe the region of interest automatically, and let the pathologist decide, using his own subjective expertise, if the region presented is adequate or needs to be manually refined. Once the meaningful areas of an image are determined, the feature extraction takes place. For each cell (and its sub-cellular components), a set of densitometric, morphometric, texture, and contextual features can be measured, with a goal of characterizing the individual cells and their interactions as comprehensively as possible.

The last step is the presentation of the raw data and compilation thereof into meaningful results and/or scores. The resulting output of an image analysis system should desirably match the form of visual and/or semi-quantitative grading systems already in use by the pathologist so as to promote consistency, to be easily applicable, or to be capable of being interpreted in routine use.

The platform for the evaluation of tissue samples via image analysis is shifting more and more from the general-purpose image analyzer to specialized and dedicated "pathology workstations" configured for routine work. Such workstations combine tools needed to provide the pathologist with the necessary information to derive the best results possible. Central to such a workstation is the microscope, possibly equipped with robotic parts including a motorized stage, an automatic focus device, an objective changer, and a light intensity adjustment device. Different input devices, such as cameras capable of fast automatic focusing and acquisition of high resolution images, are linked to the workstation. The workstation can be part of a Local Area Network (LAN). The workstation can also support different communication protocols, so that available communication channels can be used to connect the workstation with other places in the world (Wide Area Network or WAN).

When integrated within a LAN and/or WAN, the workstation can be granted access to existing reference databases and Hospital Information Systems (HIS) such that any new cases to be examined can be compared with the pictures and accompanying information of reference cases which have been accumulated over time. In addition, images acquired from the slides under review can be complemented with the patient and case history.

The pathology workstation is preferably suited for a comprehensive tissue evaluation. Starting with information and digital pictures of the initial tissue sample, images of the slides prepared from the tissue can be taken. The patient and case information, the images themselves, and any quantitative information about the cell components of the tissue sample can all be stored in the same database.

All of the information accumulated by the workstation for one case, such as images, measurement results, patient data, preparation data, can be selected to be part of a report which can either be printed or signed out electronically via the network. The report provides a comprehensive picture of the case under evaluation and facilitates quality assurance and standardization.

During preprocessing/segmentation of the captured images, many different techniques/algorithms can be implemented for image analysis, particularly for quantitative video-microscopy in the field of cellular biology and pathology applications, by using multi-spectral imaging adapted to color cameras (i.e., RGB 3CCD cameras).

Effective analysis of microscopic images is essential in cellular biology and pathology, particularly for detection and quantification in genetic material (genes, messenger RNA) or the expression of this genetic information in the form of proteins, for example, gene amplification, gene deletion, gene mutation, number of messenger RNA molecules or protein expression analyses. Gene amplification is the presence of too many copies of the same gene in one cell, wherein a cell usually contains two copies, otherwise known as alleles, of the same gene. Gene deletion indicates that less than two copies of a gene can be found in a cell. Gene mutation indicates the presence of incomplete or non-functional genes. Messenger RNAs (mRNA) are molecules of genetic information, synthesized from gene reading, that serve as templates for protein synthesis. Protein expression is the production of a given protein by a cell. If the gene coding for this protein is up regulated or too many copies of the gene or mRNA are present, the protein may be over-expressed. If the gene is down regulated or deleted, the protein expression level may be low or absent.

Normal cellular behaviors are precisely controlled by molecular mechanisms involving a large number of proteins, mRNAs and genes. Gene amplification, gene deletion, and gene mutation are known to have a prominent role in abnormal cellular behaviors through abnormal protein expression. The range of cellular behaviors of concern includes behaviors as diverse as, for example, proliferation or differentiation regulation. Therefore, effective detection and quantification in gene amplification, deletion and mutation, mRNAs levels or protein expression analyses, is necessary in order to facilitate useful research, diagnostic and prognostic tools.

There are numerous laboratory techniques dedicated to detection and quantification in gene amplification, deletion and mutation, mRNA levels or protein expression analyses. For example, such techniques include Western, Northern and Southern blots, polymerase chain reaction ("PCR"), enzyme-linked immunoseparation assay ("ELISA"), and comparative genomic hybridization ("CGH") techniques. However, microscopy is routinely utilized because it is an informative technique, allowing rapid investigations at the cellular and sub-cellular levels, which may be implemented at a relatively low cost.

When microscopy is the chosen laboratory technique, the biological samples usually first undergo specific detection and revelation preparations. Once the samples are prepared, a human expert analyzes the samples with a microscope alone or with a microscope coupled to a camera and a computer, allowing both a more standardized and quantitative study. The microscope may be configured for fully automatic analysis, wherein the microscope is automated with a motorized stage and focus, motorized objective changers, automatic light intensity controls and the like.

The preparation of the samples for detection may involve different types of preparation techniques that are suited to microscopic imaging analysis, such as, for example, hybridization-based and immunolabeling-based preparation techniques. Such detection techniques may be coupled with appropriate revelation techniques, such as, for example, fluorescence-based and visible color reaction-based techniques.

In Situ Hybridization ("ISH") and Fluorescent In Situ Hybridization ("FISH") are detection and revelation techniques used, for example, for detection and quantification of genetic information amplification and mutation analyses. Both ISH and FISH can be applied to histological or cytological samples. These techniques use specific complementary probes for recognizing corresponding precise sequences. Depending on the technique used, the specific probe may include a chemical (ISH) marker or a fluorescent (FISH) marker, wherein the samples are then analyzed using a transmission microscope or a fluorescence microscope, respectively. The use of a chemical marker or a fluorescent marker depends on the goal of the user, each type of marker having corresponding advantages over the other in particular instances.

In case of protein expression analyses, further immunohistochemistry ("IHC") and immunocytochemistry ("ICC") techniques, for example, may be used. IHC is the application of immunochemistry to tissue sections, whereas ICC is the application of immunochemistry to cultured cells or tissue imprints after they have undergone specific cytological preparations, e.g. liquid based preparations. Immunochemistry is a family of techniques based on the use of specific antibody, wherein antibodies are used to specifically target molecules inside or on the surface of cells. The antibody typically, contains a marker that will undergo a biochemical reaction, and thereby experience a color change, upon encountering the targeted molecules. In some instances, signal amplification may be integrated into the particular protocol, wherein a secondary antibody that includes the marker stain follows the application of a primary specific monoclonal antibody.

In both hybridization and immunolabeling studies, chromogens of different colors are used to distinguish the different markers. As these markers may be cell compartment specific, this a priori knowledge can be used to automatically segment the cells (i.e. separates the nucleus masks from the cytoplasmic and or membrane masks). Overall, "colorimetric" algorithms are aimed to provide sample information to ease diagnosis and/or prognosis of the particular case. For illustration, the detection and quantification of the breast ER, PR and HER2 protein expression levels may be provided using a quantitative microscopy algorithm applied to immunohistochemistry (IHC) techniques.

In light of such image analysis techniques, however, there exists a need for improvements that facilitate flexibility in such analysis while providing a pathologist with accurate and useful information for allowing the pathologist to form an appropriate diagnosis and/or prognosis.

SUMMARY OF THE INVENTION

The above and other needs are met by the present invention(s) which, in one embodiment, provides a method of staining a sample for microscopy imaging whereby the image of the stained sample is configured to exhibit an optimum contrast between sub-cellular components for diagnosis by a pathologist. Such a method comprises staining a sample with a dye; determining a transmittance value of the dye from a microscopy image of the sample; forming an artificial image of the sample from the determined transmittance value of the dye; varying the transmittance value of the dye so as to form a series of artificial images; selecting one image, from the series of images, exhibiting the optimum contrast between sub-cellular components for the dye and determining the corresponding transmittance value of the dye in the one image; and varying staining of the sample with the dye so as to provide a stained sample having the transmittance value of the dye corresponding to the optimum contrast between sub-cellular components.

Another aspect of the present invention comprises a method of artificially staining a sample. Such a method includes staining a sample with a first dye; determining a transmittance value and an extinction coefficient of the first dye from a microscopy image of the sample; forming an artificial image of the sample from the determined transmittance value of the first dye; and substituting an extinction coefficient of a second dye for the extinction coefficient of the first dye so as to artificially stain the sample with the second dye.

Still another aspect of the present invention comprises a method of obtaining measurements of a sample from an image thereof. Such a method includes selecting a region of interest in the sample from an RGB image thereof; segmenting the region of interest in the RGB image to identify any objects of interest therein; implementing feature extraction to determine measurements for the identified objects of interest; and determining cell scores with respect to at least one of marker localization and signal to noise ratio.

A further aspect of the present invention comprises a method of selecting a region of interest on a slide, wherein the region is positively contrasted from a surrounding thereof in a marker-only image corresponding to an RGB image of the sample, and the positively contrasted region includes at least one of a relatively larger nuclei and a relatively higher cell density than the surrounding. Such a method includes applying a low pass filter to a marker-only image of a sample, wherein the marker-only image is obtained through chromogen separation of the RGB image of the sample; determining a marker-only histogram of pixels in the marker-only image; and binarizing the marker-only image according to a threshold in the marker-only histogram so as to form a mask for discriminating between negative and positive regions of the sample.

Another aspect of the present invention comprises a method of segmenting a sample from an image thereof. Such a method includes determining a background component of an RGB image of the sample via a thresholding process; segmenting the image by creating a component image of at least one of a membrane, a cytoplasm, and a nucleus; refining the segmented image; and filtering any unwanted objects from the image.

Yet another aspect of the present invention comprises a method of determining optical density data for at least one dye staining a sample, for a high dye concentration, from an image obtained with a low bit resolution imaging device. Such a method includes capturing a series of images of the sample at different integration times; selecting a highest non-saturated intensity in each of a red, green, and blue channel of the imaging device; and reconstructing an optimized image of the sample using the highest non-saturated intensity levels in the red, green, and blue channels such that the optimized image is suitable for chromogen separation.

Another aspect of the present invention comprises a chromogen separation method for an image of a biological sample stained with four dyes obtained with a three channel imaging device. Such a method includes defining a priori known significant three dye combinations of the four dyes spatially collocated in the biological sample; obtaining an image of a sample stained with four dyes with an imaging device having a red, green, and blue channel, such that the image thereby includes a plurality of pixels each having a corresponding RGB triplet; projecting each RGB triplet onto an extinction coefficient plane where $Ecr+Ecg+Ecb=1$; determining the three dye combination of the four dyes in the extinction coefficient plane corresponding to each RGB triplet; and separating the image of the sample by tabulating an amount of pixels in the image corresponding to each three dye combination in the extinction coefficient plane.

Embodiments of the present invention thus meet the needs identified herein and provide significant advantages as further detailed herein.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 1 schematically illustrates a series of electronically-stained images of a sample, wherein the transmittance value of one of the dyes staining the sample is varied so as to determine the optimal marker intensity, as shown in the nucleus, allowing both a morphological read by the pathologist and a positive decision of the cell based upon the marker expression;

FIGS. 2A and 2B show some examples of automatically-selected regions of interest in accordance with one aspect of the present invention;

FIGS. 3A1-3A2 and 3B1-3B2 show examples of automatically-selected regions of interest and subsequent sub-cellular segmentation according to one aspect of the present invention;

FIG. 4 schematically illustrates a method of cell scoring according to one aspect of the present invention;

FIGS. 5A and 5B illustrate a method of analyzing samples including high dye concentrations using a time integration approach according to one aspect of the present invention;

FIGS. 6A-6D illustrate data regarding each of 4 dyes for staining a sample for a 4 dye chromogen separation procedure according to one aspect of the present invention;

Figure 8A:
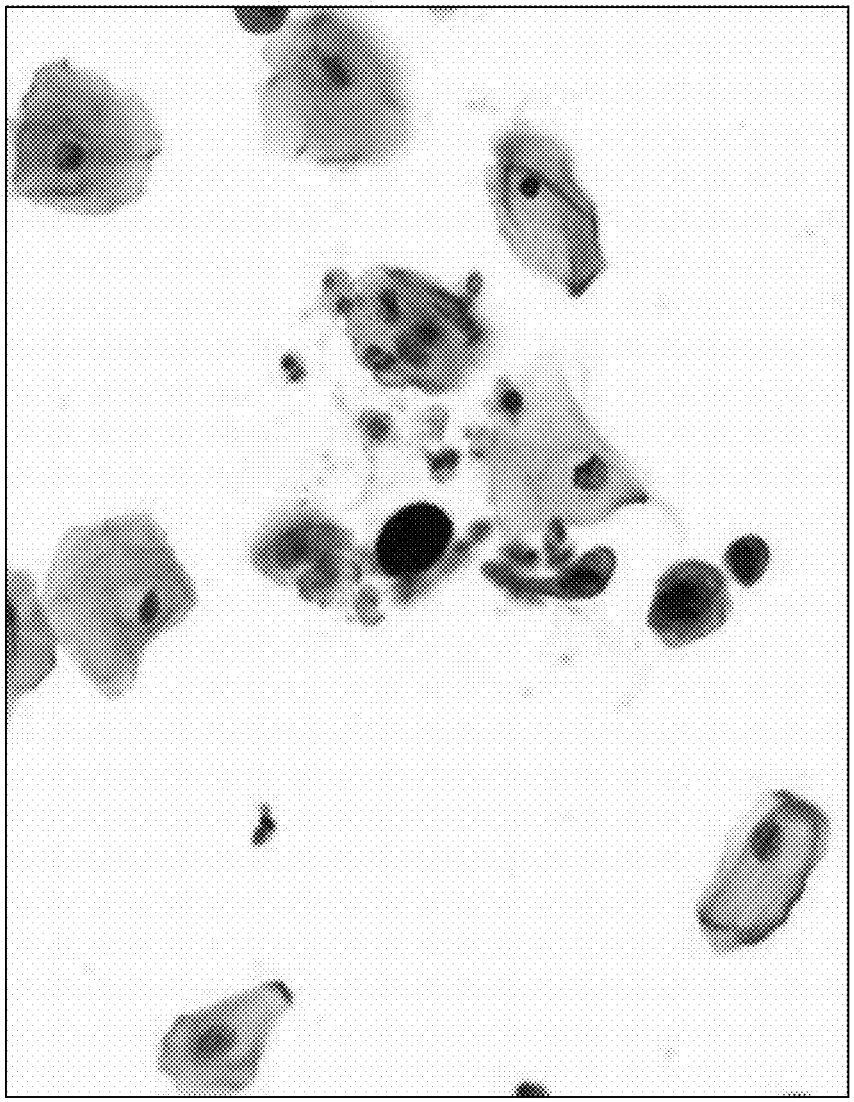
Figure 9B:
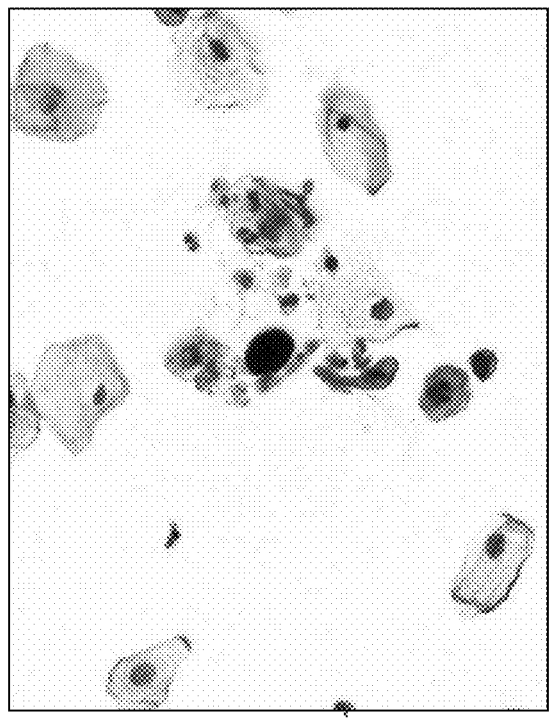
Figure 9A:
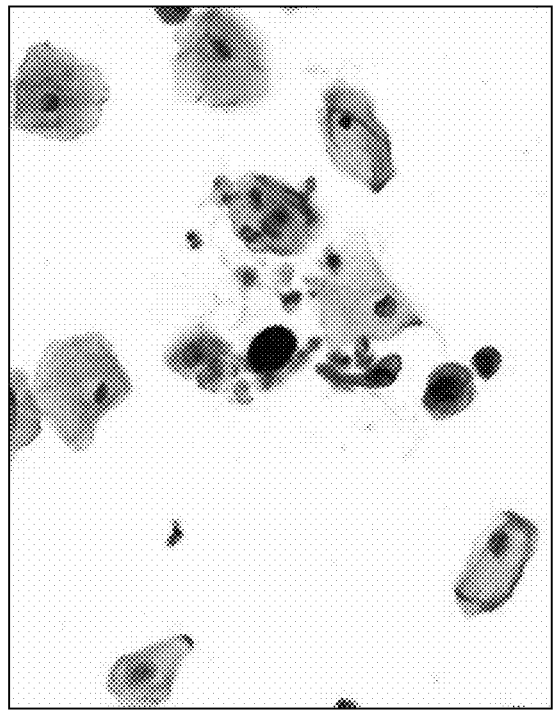
Figure 9C:
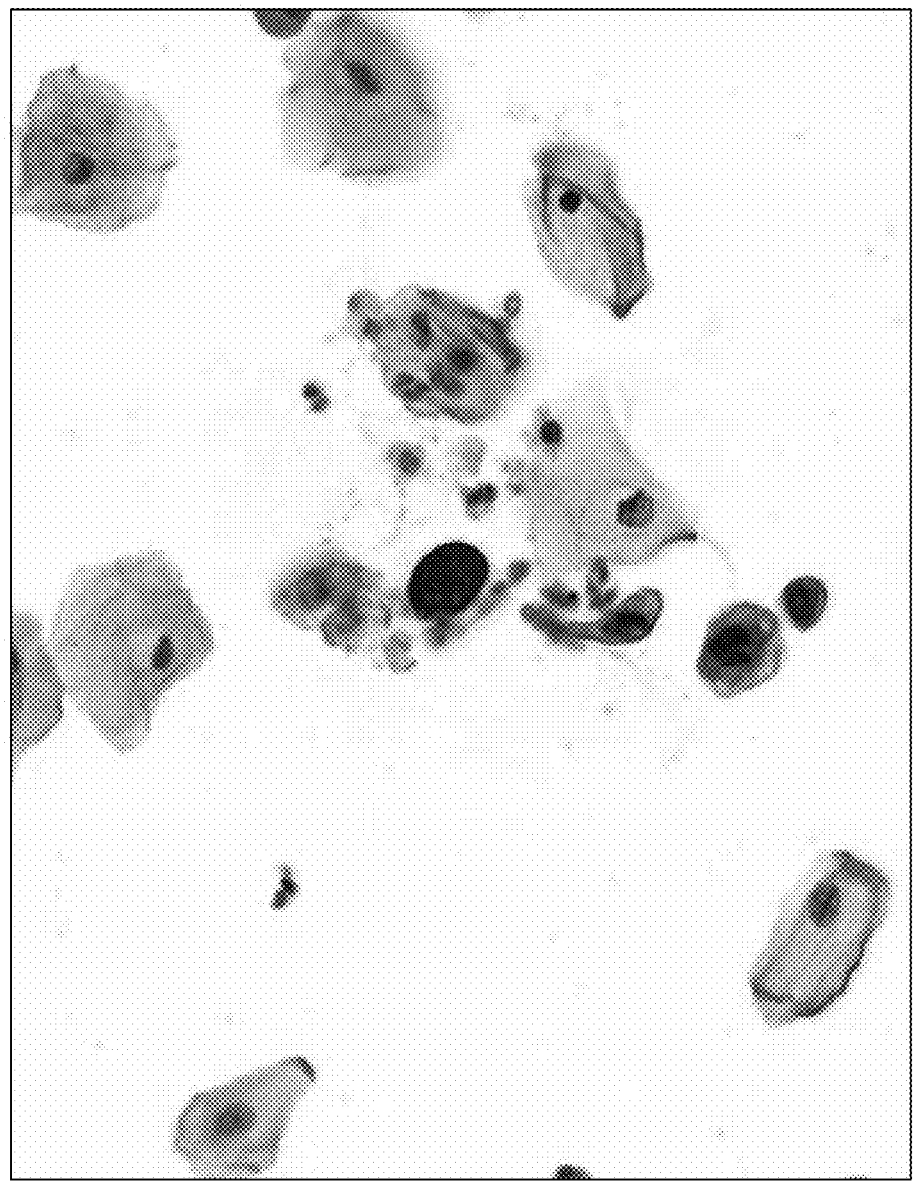

FIGS. 7A, 7B1, and 7B2 schematically illustrate the 4 dyes of FIGS. 6A-6D represented in the Maxwell equivalent extinction coefficient plane, and the 2 accepted 3 dye combinations thereof, respectively, in accordance with one aspect of the present invention;

FIG. 8A illustrates a modified PAP field of view stained with the 4 dyes of FIG. 6;

FIGS. 8B-8E illustrate the modified PAP field of view of FIG. 8A for each of the 4 dyes separately from the other dyes using extended chromogen separation; and FIG. 9A illustrates a source (RGB) field of view of a sample, while FIG. 9B illustrates a simulated e-stained sample thereof for two of the four dye components, and FIG. 9C illustrates a simulated PAP-only e-stained image of the sample reconstructed with all dye components except DAB.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The Microscope Imaging Platform

In a typical microscopy device for image acquisition and processing, the magnified image of the sample must first be captured and digitized with a camera. Generally, charge coupled device (CCD) digital cameras are used in either light or fluorescence quantitative microscopy. Excluding spectrophotometers, two different techniques are generally used to perform such colorimetric microscopic studies. In one technique, a black and white (BW) CCD camera may be used. In such an instance, a gray level image of the sample is obtained, corresponding to a monochromatic light having a wavelength specific to the staining of the sample to be analyzed. The specific wavelength of light is obtained either by filtering a white source light via a specific narrow bandwidth filter, or by directly controlling the wavelength of the light source, using either manual or electronic controls. Accordingly, using this technique, the analysis time increases as the number of colors increases because a light source or a filter must be selected for every different sample staining or every different wavelength. Therefore, many different images of the sample, showing the spectral response of the sample at different wavelengths, must be individually captured in a sequential order to facilitate the analysis. When multiple scenes or fields of view must be analyzed, the typical protocol is to automate the sequence in a batch mode to conserve processing time.

According to a second technique, a color CCD digital camera is used, wherein three gray level images of the sample are simultaneously captured and obtained. Each gray level image corresponds to a gray level image in each of the respective Red, Green and Blue channel (RGB) of the color CCD camera. When a color CCD digital camera is used, wherein three gray level images of the sample are simultaneously captured and obtained (each gray level image corresponds to a gray level image in each of the respective Red, Green and Blue channel (RGB)), chromogen separation techniques can be applied, which may allow the optical density of each molecular species (revealed by their associated chromogen or dye) to be evaluated in any location of the image (pixel). On the biological sample, markers and counter stains generally indicate the dyes to detect and quantify.

According to an arising third technique (e.g., using a JUMBOSCAN multispectral camera by Lumiere Technology), up to 13 gray level images of the sample can be simultaneously captured and obtained. This type of camera/scanner could increase the potential of chromogen separation techniques in the future by increasing the number of dyes that can be simultaneously solved for a given sample.

Regardless, the concentration of the molecular specie can be determined from a color image of the sample, where the color image includes 3 or more channels. In a video-microscopy system equipped with a 3CCD camera, the image should desirably be balanced and normalized according to an empty field white reference and a black field image, and then corrected for shading. Furthermore, the image should desirably be spatially corrected for chromatic aberrations, channel by channel. An optical density of the sample can then be computed in each of the red, green, and blue channels of the RGB image, at a particular pixel in the image, from the measured transmitted light. A corresponding optical density vector is thereafter formed for that pixel. The optical density vector is then multiplied by the inverse of a relative absorption coefficient matrix of the dyes present in the sample so as to form a resultant vector for the pixel, representing the optical density contributions from each dye. The relative absorption coefficient matrix comprises a relative absorption coefficient for each of the dye (marker(s) and counter stain(s)) used in the sample preparation protocol, in each of the red, green, and blue channels. The resultant vector thus comprises the concentration of the molecular species, as indicated by the marker(s), and by the counter stain(s), for that pixel.

Such imaging techniques, also known as multi-spectral imaging techniques, when adapted to color imaging (RGB camera), allow a real time (video rate) processing of the sample (typically 40 millisecond per frame), which provides a considerable advantage. In effect, for speed issues and real time processing, or displaying purposes in case of the use of an RGB camera, the acquisition through the different channels is performed in parallel and look-up tables (LUT) can be generated which map the RGB color input values to pre-computed concentrations and/or transmittance of each of the participating dyes.

Such techniques are discussed in more detail, for example, in U.S. Patent Application Publication Nos. US 2003/0091221A1 (Method for quantitative video-microscopy and associated system and computer software program product) and US 2003/0138140A1 (Method for quantitative video-microscopy and associated system and computer software program product), both to Marcelpoil et al. and assigned to Tripath Imaging, Inc, also the assignee of the present invention, the contents of which are incorporated herein in their entirety by reference.

The Lambert-Beer Law

The microscopic imaging platform is configured to analyze the sample in accordance with the Lambert-Beer law. The Lambert-Beer law generally describes a proportionality that can be observed between the concentration of molecules in a solution (the concentration of the "molecular specie" or the "sample") and the light intensity measured through the solution. The Lambert-Beer law is typically expressed as:

$$OD = \epsilon \cdot l \cdot C \quad (1)$$

OD is the optical density of the solution, $\epsilon$ is the proportionality constant called molar extinction or absorption coefficient, l is the thickness of the sample, and C is the concentration of the molecular specie. The absorption coefficient $\epsilon$ is specific to the molecular specie and is typically expressed in units of $L \cdot mol^{-1} \cdot cm^{-1}$.

This proportionality relationship defined by the Lambert-Beer law has been verified under the several conditions including, for example, monochromatic light illuminating the sample, low molecular concentration within the sample, generally no fluorescence or light response heterogeneity (negligible fluorescence and diffusion) of the sample, and lack of chemical photosensitivity of the sample. The Lambert-Beer law may have additional requirements, however, such as, for instance, correct Koehler illumination of the sample under the microscope.

Koehler illumination is offered on almost all state-of-the-art microscopes, and provides even illumination in the image plane, while allowing for effective contrast control. Koehler illumination is typically critical for densitometry analysis. Correct Koehler illumination is provided, for example, by a two-stage illuminating system for the microscope in which the source is imaged in the aperture of the sub-stage condenser by an auxiliary condenser. The sub-stage condenser, in turn, forms an image of the auxiliary condenser on the object. An iris diaphragm may also be placed at each condenser, wherein the first iris controls the area of the object to be illuminated, and the second iris varies the numerical aperture of the illuminating beam.

The Lambert-Beer law has an additive property such that, if the sample comprises several light-absorbing molecular species, for example, $s_1$ and $s_2$, having respective concentration $C_1$ and $C_2$, the OD of a sample of thickness l (in solution, $l_1=l_2=l$) can be expressed as:

$$OD = \epsilon 1 \cdot l1 \cdot C1 + \epsilon 2 \cdot l2 \cdot C2 \tag{2}$$

This situation may occur, for example, in a biological analysis where a "scene" or field of view or portion of the sample has been stained with two dyes consisting of a marker dye for targeting the molecular specie of interest and a counter stain for staining the remainder of the sample.

Correction of Chromatic Aberration

To accurately measure the concentration of given species imaged under a microscope, the measurements of the optical densities performed at different wavelengths should correspond to the same portion of the sample. That is, the system can be physically corrected for chromatic aberration or, otherwise, the correction can be made through another methodology such as software.

The natural dispersion power of glass causes a simple lens to focus blue light at a shorter distance than red light. That is, a simple lens has different focal lengths for light of different wavelength (different colors). Two phenomena occur as a direct consequence:

1) The difference in position along the vertical axis of the focal points for light of different wavelength is called longitudinal chromatic aberration. That is, when focusing the image for a given color (green, for example), the images corresponding to the other colors tend to be slightly out of focus (blue and red, in this example, will appear out of focus).

2) The difference in magnification (focal length) for light of different wavelengths is called lateral chromatic aberration. That is, the image of a blue (short) wavelength will appear larger than the image of a red (large) wavelength.

In systems with high quality objectives (apochromatic objectives), chromatic aberration is corrected. If chromatic aberration is otherwise structurally not well corrected, a software-based method for correcting lateral chromatic aberration can be implemented as follows:

1) Determine the coordinate of the objective center as compared to the camera chip center;
2) Evaluate the observed magnification factor for each wavelength as compared to an arbitrary chosen wavelength (usually the central wavelength, i.e., green if using an RGB camera); and
3) Resample each image according to its relative magnification and the coordinate of the objective center.

Performing Chromogen Separation

Once the microscope has been set in Koehler illumination mode for image acquisition, and any chromatic aberrations have been addressed or apochromatic objectives used, the additive property of the Lambert-Beer law can be used to perform chromogen separation using linear algebraic equations.

More particularly, the additive property of the Lambert-Beer law can also be expanded to a situation in which the scene is analyzed in a color image environment, such as, for example, generated by a RGB camera having separate red, green, and blue channels. In such an example, the marker dye (or "dye 1") would exhibit absorption coefficients, $\epsilon_{1r}$, $\epsilon_{1g}$, and $\epsilon_{1b}$, in the red, green and blue channels, respectively. Note that the analysis of the image in each of the red, green, and blue channels essentially comprises analyzing a red representation of the image across the red spectrum, a green representation of the image across the green spectrum, and a blue representation of the image across the blue spectrum. Accordingly, the counter stain (or "dye 2") would exhibit absorption coefficients, $\epsilon_{2r}$, $\epsilon_{2g}$, and $\epsilon_{2b}$, in the red, green and blue channels, respectively. Therefore, according to the additive property of the Lambert-Beer law, analysis of the sample in the RGB environment would lead to the system of three equations for the optical density thereof:

$$OD_r = \epsilon_{1r} \cdot l_1 \cdot C_1 + \epsilon_{2r} \cdot l_2 \cdot C_2 \tag{3}$$

$$OD_g = \epsilon_{1g} \cdot l_1 \cdot C_1 + \epsilon_{2g} \cdot l_2 \cdot C_2 \tag{4}$$

$$OD_b = \epsilon_{1b} \cdot l_1 \cdot C_1 + \epsilon_{2b} \cdot l_2 \cdot C_2 \tag{5}$$

where $OD_r$, $Od_g$, and $OD_b$ represent the optical densities of the sample measured in the red, green and blue channels, respectively. Still further, in the case of increased sample preparation complexity such as, for example, the treatment of the sample with three different dyes, equations (3), (4), and (5) become:

$$OD_r = \epsilon_{1r} \cdot l_1 \cdot C_1 + \epsilon_{2r} \cdot l_2 \cdot C_2 + \epsilon_{3r} \cdot l_3 \cdot C_3 \tag{6}$$

$$OD_g = \epsilon_{1g} \cdot l_1 \cdot C_1 + \epsilon_{2g} \cdot l_2 \cdot C_2 + \epsilon_{3g} \cdot l_3 \cdot C_3 \tag{7}$$

$$OD_b = \epsilon_{1b} \cdot l_1 \cdot C_1 + \epsilon_{2b} \cdot l_2 \cdot C_2 + \epsilon_{3b} \cdot l_3 \cdot C_3 \tag{8}$$

In such a situation, the three dyes may comprise, for instance, one marker dye and two counter stains, or two marker dyes and one counter stain, or even three separate marker dyes. This property of the Lambert-Beer law might be expanded to include an even greater plurality of dye combinations. However the chromogen separation procedure described herein focuses on making use of a fast color-image capture device with 3 channels, such as for example a 3CCD RGB camera, for multi-spectral imaging of biological markers. Therefore, due to the 3 distinct information channels (R, G, B) only three equations can be used in any location.

In applying the Lambert-Beer law to a digital microscopy system, it is difficult and complex, inaccurate, or sometimes not possible to measure the thickness l of the sample. Consequently, the concentration C of the molecular specie can be extended and examined as the product of l and C (l·C), and the results treated accordingly. For example, where the concentration of one dye is being compared to the concentration of another dye in a particular sample, the sample thickness term will be common to both concentrations and thus it becomes less important to determine the sample thickness as an absolute and accurate value. Therefore, it will be understood that an accurate determination of the thickness is usually not required, but assumed constant and therefore generally negligible in the analysis disclosed herein.

The application of the Lambert-Beer law to the digital microscopy system also recognizes that the Lambert-Beer law can be expressed as:

$$OD_{(x,y)} = \log I_{0(x,y)} - \log I_{(x,y)} \tag{9}$$

for a digital image of the sample, where (x,y) signifies a particular pixel in the image, $OD_{(x,y)}$ is the optical density of the sample at that pixel, $I_{(x,y)}$ is the measured light intensity or transmittance of the sample at that pixel, and $I_{0(x,y)}$ is the light intensity of the light source as measured without the light-absorbing sample. Accordingly:

$$IOD = \frac{1}{N} \Sigma (\log I_{0(x,y)} - \log I_{(x,y)}) \qquad (10)$$

where IOD is the integrated optical density of the digital image of the sample, and N is the number of pixels in the surface image of the sample. A proportionality constant may be appropriately considered where relative comparisons are drawn in light intensities. Further, in quantitative microscopy according to the Lambert-Beer law, the proportionality relationship between the optical density OD of the sample and the dye concentrations is conserved.

Therefore, for a prepared sample examined by the digital microscopy system, the appropriate relation is expressed as:

$$\ln I_0 - \ln I = \ln I_0/I = OD = \epsilon \cdot l \cdot C \qquad (11)$$

Where, for example, an 8 bit RGB camera is used in the system, the light intensity transmitted through the sample will be expressed as $2^8$ (=256) values between 0 and 255. For example, the initial intensity $I_o$ of the light source, which corresponds to 100% transmittance, will be expressed as values close to 255 (representing the brightest possible value) in each of the red, green, and blue channels. Indeed, the operator adjusts the camera frame grabber/light source so that a pure "white" light in absence of the sample, corresponding to 100% transmittance, would have an intensity value close to 255 in each of the red, green, and blue channels, whereas in the absence of light, corresponding to 0% transmittance, the "black image" will have an intensity value close to 0 in each of the red, green, and blue channels. At any pixel, 100% transmittance, $I_o$, is therefore expressed as the difference between the value measured by the camera in presence of the light source, minus the value measured by the camera in absence of the light source, for each of the red, green, and blue channels. Because the intensity of the light source may vary spatially over the measured field of view, and because the optics may heterogeneously absorb light, 100% transmittance may correspond to different dynamic ranges over the measured field of view. The OD of the sample is expressed (11) as the logarithm of the ratio of the transmittance in absence of the sample ($I_o$), and transmittance in presence of the sample (I), and is therefore largely spatially independent of the small variations in the real dynamic range measured at 100% transmittance.

Since the light source intensity remains substantially constant over time, or can be easily re-evaluated, the reading of the light intensity in any pixel can therefore be translated into a measure of the relative transmittance at the pixel location for each of the red, green, and blue channels. Once $I_o$ and I are known, the corresponding OD can be computed.

Any location on the field of view where a unique dye is present (the only absorbing material) allows the relative extinction coefficients of the dye to be measured for the different RGB channels. Because in equation (1), $l \cdot C$ is equal for each of the RGB channels at a given location, if both l and C are known at this particular location the exact extinction coefficient can be computed as being $OD/(l \cdot C)$. The absorption coefficient $\epsilon$ in each of the red, green, and blue channels can thus be consequently extracted as being:

$$\epsilon_r = OD_r/(l \cdot C) = (\ln(I_{or}/I_r))/(l \cdot C) \qquad (12)$$

$$\epsilon_g = OD_g/(l \cdot C) = (\ln(I_{og}/I_g))/(l \cdot C) \qquad (13)$$

$$\epsilon_b = OD_b/(l \cdot C) = (\ln(I_{ob}/I_b))/(l \cdot C) \qquad (14)$$

Unfortunately, ($l \cdot C$) is usually unknown and therefore, the extinction coefficients $\epsilon$ are computed arbitrarily, as being the ratio of the OD measured at the given pixel in the considered channel and the maximum OD measured at this location for any of the RGB channels (the determination of the absorption coefficient $\epsilon$ in each of the red, green, and blue channels in absence of a priori knowledge concerning ($l \cdot C$) is a matter of linear equation manipulation in order to achieve a relative solution where l and C are arbitrarily set to 1), wherein:

$$\epsilon_r = OD_r/1 = OD_r = \ln(I_{or}/I_r) \qquad (13)$$

$$\epsilon_g = OD_g/1 = OD_g = \ln(I_{og}/I_g) \qquad (14)$$

$$\epsilon_b = OD_b/1 = OD_b = \ln(I_{ob}/I_b) \qquad (15)$$

Consequently if the absolute concentration of the dye remains unknown, it is still possible to compute arbitrary (or relative) dye concentrations in any pixel, with a known absolute error factor equal to ($l \cdot C$).

Because l is unique at a given pixel location and can arbitrarily be set to 1, equations 6, 7, and 8 may be rewritten as follow where $C_1$, $C_2$ and $C_3$ are related to l.

$$OD_r = \epsilon_{1r} \cdot C_1 + \epsilon_{2r} \cdot C_2 + \epsilon_{3r} \cdot C_3 \qquad (16)$$

$$OD_g = \epsilon_{1g} \cdot C_1 + \epsilon_{2g} \cdot C_2 + \epsilon_{3g} \cdot C_3 \qquad (17)$$

$$OD_b = \epsilon_{1b} \cdot C_1 + \epsilon_{2b} \cdot C_2 + \epsilon_{3b} \cdot C_3 \qquad (18)$$

When all the extinction coefficients have been evaluated for different dyes, and optical densities are known from the reading of the image data, solving these equations to extract $C_1$, $C_2$ and $C_3$ just involves solving a set of linear equations.

Solution of Linear Algebraic Equations/Matrices

A set of linear algebraic equations appear, for example, as:

$$a_{11}x_1 + a_{12}x_2 + a_{13}x_3 + \ldots + a_{1N}x_N = b_1 \qquad (19)$$
$$a_{21}x_1 + a_{22}x_2 + a_{23}x_3 + \ldots + a_{2N}x_N = b_2$$
$$a_{31}x_1 + a_{32}x_2 + a_{33}x_3 + \ldots + a_{3N}x_N = b_3$$
$$\ldots$$
$$a_{M1}x_1 + a_{M2}x_2 + a_{M3}x_3 + \ldots + a_{MN}x_N = b_M$$

Here the N unknowns $x_j$, j=1, 2, . . . , N are related by M equations. The coefficients $a_{ij}$ with i=1, 2, . . . , M and j=1, 2, . . . , N are known numbers, as are the right-hand side quantities $b_i$, i=1, 2, . . . , M.

If M<N, there is effectively fewer equations than unknowns. In this case there can be either no solution, or else more than one solution vector x.

If N=M then there are as many equations as unknowns, and there is a good chance of solving for a unique solution set of $x_j$'s.

If M>N that there are more equations than unknowns, and there is, in general, no solution vector x to equation (1), the set of equations is said to be over determined. In such a case, the most appropriate solution will be considered in general as the one fitting the best all the equations (i.e., the solution minimizing the sum of reconstruction errors).

Equation (19) can thus be written in matrix form as $$A \cdot x = b \qquad (20)$$

Here (·) denotes matrix multiplication, A is the matrix of coefficients, and b is the right-hand side written as a column vector. By convention, the first index on an element $a_{ij}$ denotes its row; the second index its column. $a_{i.}$ or a[i] denotes a whole row a[i][j], j=1, . . . , N.

The solution of the matrix equation A·x=b for an unknown vector x, where A is a square matrix of coefficients, and b is a known right-hand side vector, usually requires the determination of $A^{-1}$ which is the matrix inverse of the matrix A.

$$x = A^{-1} \cdot b \qquad (21)$$

$A^{-1}$ which is the matrix inverse of matrix A, i.e., $A \cdot A^{-1} = A^{-1} \cdot A = 1$, where 1 is the identity matrix. In one particular case, experimental conditions are set up so that there are more (or equal number) equations than unknowns, M≥N. When M>N occurs, there is, in general, no solution vector x to equation (19), and the set of equations is said to be over determined. Frequently, however, the best "compromise" solution is one that comes closest to satisfying all equations simultaneously. If closeness is defined in the least-squares sense (i.e., that the sum of the squares of the differences between the left- and right-hand sides of equation (19) are minimized), then the over determined linear problem reduces to a (usually) solvable linear problem, also referred to as the linear least-squares problem, that can be solved using singular value decomposition (SVD). SVD involves the parametric modeling of data, and is one method for solving most linear least-squares problems. (NUMERICAL RECIPES IN C: THE ART OF SCIENTIFIC COMPUTING (ISBN 0-521-43108-5) Copyright (C) 1988-1992 by Cambridge University Press. Programs Copyright (C) 1988-1992 by Numerical Recipes Software.).

In applying these concepts to the present case, the determination of the absorption coefficient ε matrix for different dyes may be performed independently of sample evaluation and stored for further application to samples treated with at least one of the respective dyes. Computing solutions for all possible pixel values allows substantially real time processing. Since, in the chosen example of an 8 bit 3CCD color image acquisition device, the measured light intensity I of a sample ranges between limits of 0 and 255 in each of the red, green, and blue channels, all possible gray values (with respect to the original light intensity $I_o$) may be pre-computed ($256^3$ in case of an 8 bit RGB system) and stored, for example, within the computer. Thus, for a sample stained with a particular dye, the transmitted light intensity I (or the optical density OD) can be measured at a pixel in each of the red, green, and blue channels and then compared to the previously stored gray values and the absorption coefficients matrix for that particular dye to thereby determine the dye concentration C (or an estimate thereof as the product l·C) at that pixel. In this regard, there are [256(red)×256(green)×256(blue)]=$256^3$ solutions to compute, giving rise to a 16 megabyte (raw data) look-up table (LUT) for each of the dyes. Gray value resolutions exceeding 8 bits per channel will lead to larger LUTs (i.e., >1 gigabyte if 10 bits per channel).

Electronic Staining

According to one aspect of the present invention, gray levels or RGB transmittance values of an artificial image resulting from any combination of the previously-examined dyes can be generated since there are not anymore unknown variables. As such, for a particular pixel and its solved dye concentrations, the single dye images would correspond to the following Black and White (BW) or RGB pixel intensities:

$$OD_{BW} = C \text{ and } I_{BW} = \mathrm{Exp}(\ln(I_o) - OD_{BW}) \qquad (22)$$

$$OD_r = \epsilon_r \cdot C \text{ and } I_r = \mathrm{Exp}(\ln(I_o) - OD_r) \qquad (23)$$

$$OD_g = \epsilon_g \cdot C \text{ and } I_g = \mathrm{Exp}(\ln(I_o) - OD_g) \qquad (24)$$

$$OD_b = \epsilon_b \cdot C \text{ and } I_b = \mathrm{Exp}(\ln(I_o) - OD_b) \qquad (25)$$

When this process is applied to each pixel of a captured digital image, an artificial picture of the same field of view can be generated using only the respective contribution of any of the constituent dyes. As such, if the extinction coefficients of one dye are exchanged with the extinction coefficients of another dye, it is then possible to simulate how the same artificial image corresponding to a given marker only would be seen through a microscope, if the dye used to reveal this marker is changed to a secondary dye.

Figure 1:
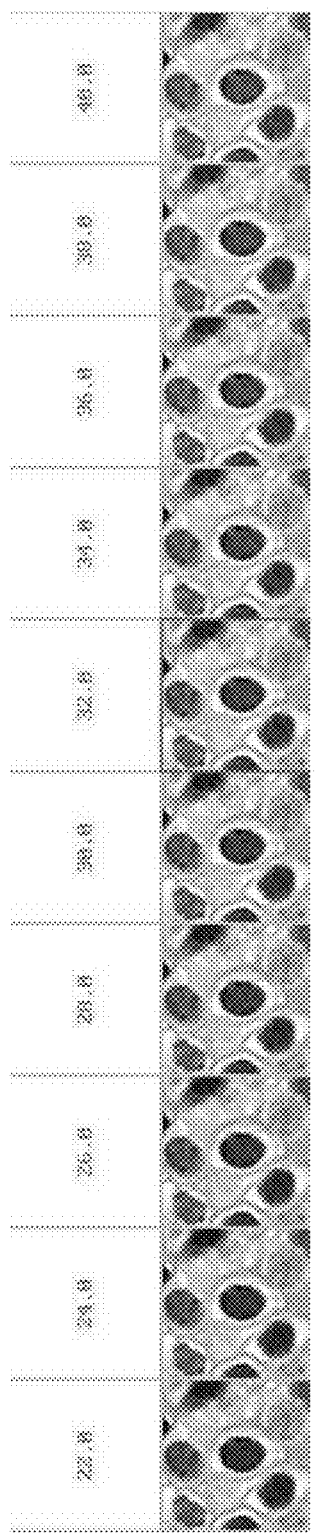

Furthermore, using the additive property of the Lambert-Beer law, it is also possible, as shown in FIG. 1, to generate an artificial image where the relative contributions of each dye are changed, for example, using absolute weighting coefficients or relative weighting coefficients (see equation 26-28 for a 2 dye electronically stained ("e-stained") image where the RGB image is reconstructed after changing the Dye 1 and Dye 2 proportions by weighting factors $w_1$ and $w_2$.

$$OD_r = w_1 \cdot \epsilon_{1r} \cdot C_1 + w_2 \cdot \epsilon_{2r} \cdot C_2 \text{ and } I_r = \mathrm{Exp}(\ln(I_o) - OD_r) \qquad (26)$$

$$OD_g = w_1 \cdot \epsilon_{1g} \cdot C_1 + w_2 \cdot \epsilon_{2g} \cdot C_2 \text{ and } I_g = \mathrm{Exp}(\ln(I_o) - OD_g) \qquad (27)$$

$$OD_b = w_1 \cdot \epsilon_{1b} \cdot C_1 + w_2 \cdot \epsilon_{2b} \cdot C_2 \text{ and } I_b = \mathrm{Exp}(\ln(I_o) - OD_b) \qquad (28)$$

More particularly, FIG. 1 illustrates an estrogen receptor (ER) example in which a series of images of the same cell (original image at a determined transmittance of about 32% is shown surrounded in red) in which the amount of a marker (Brown DAB) is changed electronically (artificially), after chromogen separation, from about a 22% transmittance to about a 40% transmittance, without changing the hematoxylin content. In this manner, an optimum contrast between sub-cellular components can be determined from the artificial images, as well as the amount of the dye necessary to provide the transmittance value corresponding to the optimum contrast between marker-specific targeted and non-targeted sub-cellular components.

Measurement Strategy

According to another aspect of the present invention, a measurement strategy can be based upon and can make use of the chromogen separation technique(s) described above in many aspects, from allowing only the marker of interest to be specifically measured, to the e-staining capabilities which allow segmentation-optimized contrasted images to be generated.

Obtaining measurement results from the acquired image includes several steps: 1) selecting the region of interest (tumor region); 2) segmentation to identify the objects of interest in the image; and 3) feature extraction to calculate the various measurement features for the identified objects and affect cell scores based upon, for example, their marker localization and signal to noise ratio.

1) Region of Interest Pre-Selection

In order to reduce the workload for the pathologist, a pre-selection methodology was developed for automatically delineating the potential region of interest within the field of view that will be the region used for analysis, wherein any excluded part is thus excluded from the analysis. Such a pre-selection methodology generally requires two a priori factors:

The region of interest is positively contrasted from the surrounding when looking at the marker-only image.

Cancer targets epithelial cells which differ from the stroma cells by, for example, a larger nucleus and higher cell density.

Figure 2A:
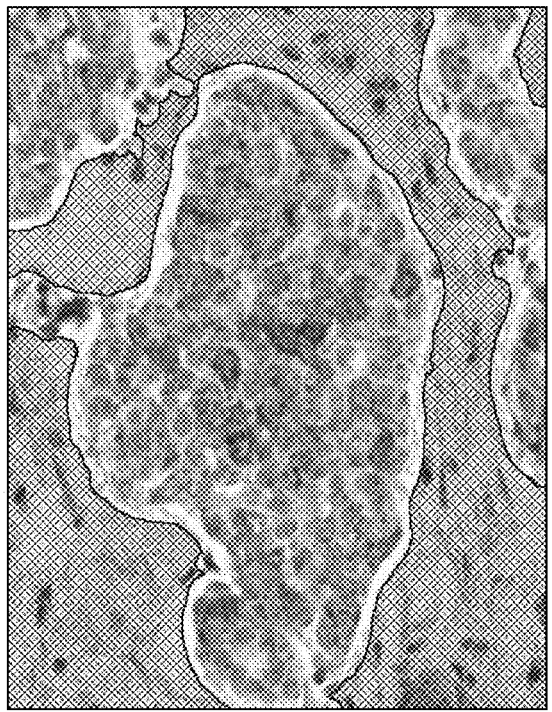
Figure 2B:
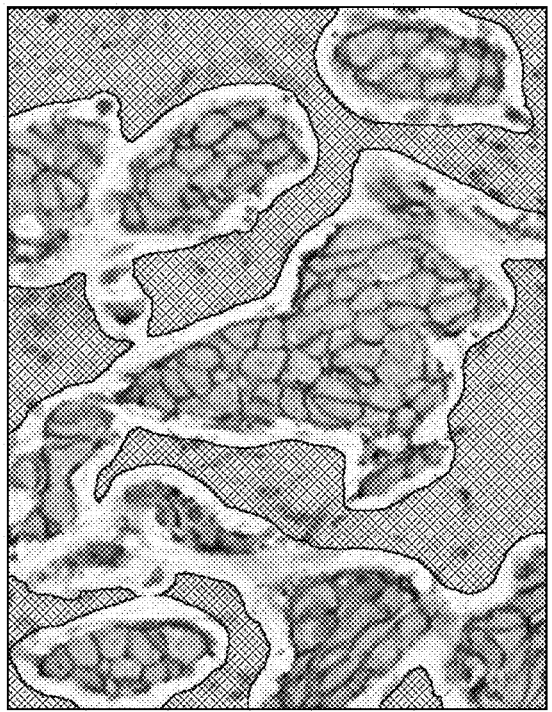

Consequently, a large low pass filter may be applied to the marker-only image resulting from the chromogen separation technique(s) applied to the RGB field of view. The marker-only histogram is measured (avoiding background regions based upon the luminance image), and then the image is binarized according to the best threshold in the histogram that could discriminate two classes (negative and positive regions). Any small holes are filled to smooth the final mask. The mask is outlined on the top of the original RGB field of view image to allow acceptance/rejection by the pathologist, as shown in FIGS. 2A and 2B. More particularly, FIG. 2A illustrates a PSMB9 example and FIG. 2B illustrates a HER2 example of automatic definition of the region of interest according to one embodiment of the pre-selection methodology disclosed herein. The region of interest is automatically computed or otherwise determined, and can be presented to the pathologist for final refinement and/or approval. If the pathologist rejects the proposed mask, drawing tools allow the pathologist to manually select the appropriate region of interest.

2) Segmentation Strategy

The segmentation strategy includes the following steps:
Background determination
Cell component image creation
Membrane segmentation*
Nucleus segmentation
Cytoplasm segmentation
Segmentation refinement
Filtering of unwanted objects

* In the case of membrane markers, such as Her2, an additional specific step of membrane segmentation is performed.

Various examples of such segmentation are shown, for example, in FIGS. 3A1-3A2 and 3B1-3B2, respectively. More particularly, FIG. 3A1 shows a PSMB9 (cytoplasmic marker) example of automatic definition of the region of interest followed by sub-cellular segmentation in FIG. 3A2. Within the region of interest, automatically defined cells have been segmented, such that the nucleus masks appear in blue and the cytoplasm boundaries appear in red, while background pixels are shown in black. FIG. 3B1 illustrates a HER2 (membrane marker) example of automatic definition of the region of interest followed by sub-cellular segmentation in FIG. 3B2. Within the region automatically defined, cells have been segmented, such that nucleus masks appear in blue and the membrane appears in green, while background pixels are shown in black. One skilled in the art will appreciate, however, that additional image processing steps or refinements may, in some instances, be needed to adapt such generic algorithms to tissue or marker specificities.

2a) Background Determination

The first segmentation step is to divide the image content into fore- and background. Since the imaging platform is designed to support bright field microscopy, objects will appear darker than the bright background. To create a background mask for an image, the image is converted into a luminance image and a background threshold level is calculated. Every pixel having a luminance value above the background threshold level is considered to belong to the background. Conversely, any pixel with luminance less than the threshold belongs to the foreground which has to be processed further in the following steps.

Determining this background threshold value involves smoothing the luminance image and calculating the histogram of the smoothed image. The histogram is then scanned, beginning at the higher end, for a local minima to be used for the threshold value. The search is limited when an arbitrary 90% transmission is reached, which translates, for the case of 8-bit images, into the value of 230.

2b) Cell Component Image Creation

In the next segmentation step, cell component images for the nucleus and cytoplasm are created using chromogen separation techniques previously described. The separation is initiated according to the specification of the optical density contribution of each dye to the specific cell component. Those component images are then used as input for subsequent nucleus and cytoplasm segmentation steps. The component images are based upon e-staining capabilities and generate images which best contrast the targeted cell compartment from neighboring regions.

2c) Membrane Segmentation

Membrane segmentation is performed using the following steps:

Find the average value over the entire image that is not background.

Fill any location in the image with this mean value, if the local value is brighter.

Find the membrane by generating the image difference between large and small smoothing convolution kernels.

Binarize the resulting contrast image based upon the measured local contrast.

Extract the skeleton of the candidate membrane masks.

Delete any skeleton piece smaller than a requested minimal length.

Expand the skeleton of the membrane masks by one pixel in any direction and keep only membrane masks that fall underneath the skeleton.

Membrane segmentation is performed first to facilitate further nucleus segmentation, since membranes are generally expected to separate nuclei from one another.

2d) Nucleus Segmentation

In the beginning of the nucleus segmentation process, both the mean and median pixel values of the nucleus component image are calculated under consideration of the background mask. The greater of those values is used to create an initial nucleus mask through thresholding the nucleus component image with this value. Any pixel having a value higher than this threshold is set to the threshold value so that only pixels having a lower value remain with their original value in this initial nucleus mask. If membrane masks are available, any potential nucleus mask pixel falling within a membrane mask is deleted.

This preliminary or initial nucleus mask is then low-passed with a kernel of 1.5 times the expected nucleus size to prepare the initial nucleus mask for a watershed transformation or segmentation procedure. The output of the watershed segmentation procedure is combined with the initial nucleus mask so that only mask pixels are set where the watershed image has catchment basins and the initial nucleus mask has a pixel value below the threshold value. The resulting nucleus mask is then finalized by a clean-up step including filling holes having an area less than about one-fifth of the expected nucleus size, and removing objects that are smaller than about one-fourth of the expected nucleus size.

2e) Cytoplasm Segmentation

The cytoplasm segmentation process uses a two-way approach to create the cytoplasm mask. Both ways use the nucleus mask created in the previous step as the starting point. First, the nucleus mask is inverted and distance-transformed. The first potential cytoplasm mask is created by binarizing the output of the distance transform such that all pixels within the expected cell size are included in the resulting mask. In order to mask only the foreground, the resulting first potential cytoplasm mask is then combined with the background mask. For the second potential cytoplasm mask, the nucleus mask is again inverted and then watershed-transformed. Both the first and second potential cytoplasm masks are then combined to create the final cytoplasm mask.

2f) Segmentation Refinement

Once both the nucleus and cytoplasm segmentation masks have been established, those masks are further refined using the knowledge of the combined masks. Starting with the cytoplasm mask, each segmented object in the cytoplasm mask is identified and is associated with a labeled image, wherein each object is identified by a unique pixel value. Due to the watershed transformation in the cytoplasm segmentation, the labeled objects are separated from each other. As such, the labeled image is dilated once in order to reconnect the labeled objects.

The labeled image is then used to refine the nucleus mask. That is, each labeled object is binarized using an individual threshold. For each labeled object, the process is as follows:

Calculate the histogram for each pixel belonging to the labeled object and determine the mean pixel value.

Determine an upper and lower bound for the threshold search. The upper bound is determined by integrating the histogram starting from the upper limit until 20% of the object area is accumulated. The lower bound is determined in a similar way by integrating the histogram from the lower limit until also 20% of the expected nucleus size is accumulated.

If the lower bound is less than the upper bound, the threshold is calculated by applying Fisher discriminate analysis to the range of values in the histogram between the boundaries; otherwise, the threshold is the mean value of the upper and lower bounds.

Redraw the object into the nucleus mask by binarizing the nucleus component image using the just-determined threshold value.

Next, holes in the nucleus mask having an area smaller than about one-fifth of the expected nucleus size are filled. To prevent under-segmentation, the mask is first distance transformed and then watershed transformed to split up potentially merged nuclei.

Finally, the nucleus mask is cleared of artifacts by removing all objects smaller than about one-third of the expected nucleus size. Once the refined nucleus mask is determined, the cytoplasm segmentation procedure is repeated and results in a refined cytoplasm mask.

For Her2neu segmentation, an additional step of membrane removal is performed, which deletes any membrane mask located within about 3 pixels of a nucleus mask, so as to facilitate discrimination of a cell membrane from a nucleus membrane.

2g) Filtering of Unwanted Cells

The last processing step in the segmentation procedure involves filtering of unwanted cells. For this procedure, each object in the refined cytoplasm mask is labeled. Also, the acquired FOV image is chromogen separated into the dye images for the marker and the counter stain. For each identified object, a bounding rectangle is determined and, if the object is positioned closer than a certain distance to any image border, the object is no longer taken into account and discarded so as to prevent processing of cells extending beyond the image border. If the cell passes this criterion, its key measurement features, such as densitometry, texture, shape, contextual information, are calculated. Further examples (non-inclusive) include:

Area
Perimeter
Center of Gravity (CoG)
Minimum OD
Mean OD
Maximum OD

Each feature is computed for the nucleus, the cytoplasm, and/or the entire cell, as well as for each of the luminance, marker dye(s) and counter stain dye(s).

Using the mean transmittance determined from the Mean OD, another pass/fail criterion is applied to the cell. That is, if the cell's mean transmittance is higher than a threshold value specified in the segmentation setup, the cell is not considered any further and discarded.

3a) Cell Scoring

Based upon the features evaluated for each cell, a score can be attributed to that cell depending on the marker intensity and signal to noise ratio thereof in the targeted compartment. A cell is considered positive when the marker content of that cell in the marker-specific targeted-compartment optical density (intensity) is significantly higher than in neighboring compartments. For instance, if the marker is a nucleus marker, the contrast, or signal to noise ratio, is computed from the marker-specific optical density measure in the nucleus versus the residual optical density measured over the cytoplasm. Because the background noise is not specific by definition, the overall background mean optical density is measured over all of the cytoplasm compartment of the cells within the selected region of interest.

Nucleus Marker:

$$\text{Cell SNR}=\text{NucleusMOD}/\text{CytoplasmMOD} \qquad (28)$$

To facilitate optimum correlation with the pathologist's know-how, the contrast required to designate a cell as being positive can be adapted from strong to weak, since some pathologists consider only very intense nuclei as being positive, while other pathologists consider any faint positive staining as being positive. Such a subjective positive determination based on contrast level may also be affected by the particular pathology being considered.

A cell is positive for a nucleus marker if $$\text{NucleusMOD}>\text{CytoplasmMOD}+\max[\epsilon,k(1-\text{CytoplasmMOD})] \qquad (29)$$

For ER (estrogen receptors) it was found that $\epsilon=0.02$ and $k=0.11$

For PR (progesterone receptors) it was found that $\epsilon=0.02$ and $k=0.20$

Figure 4:
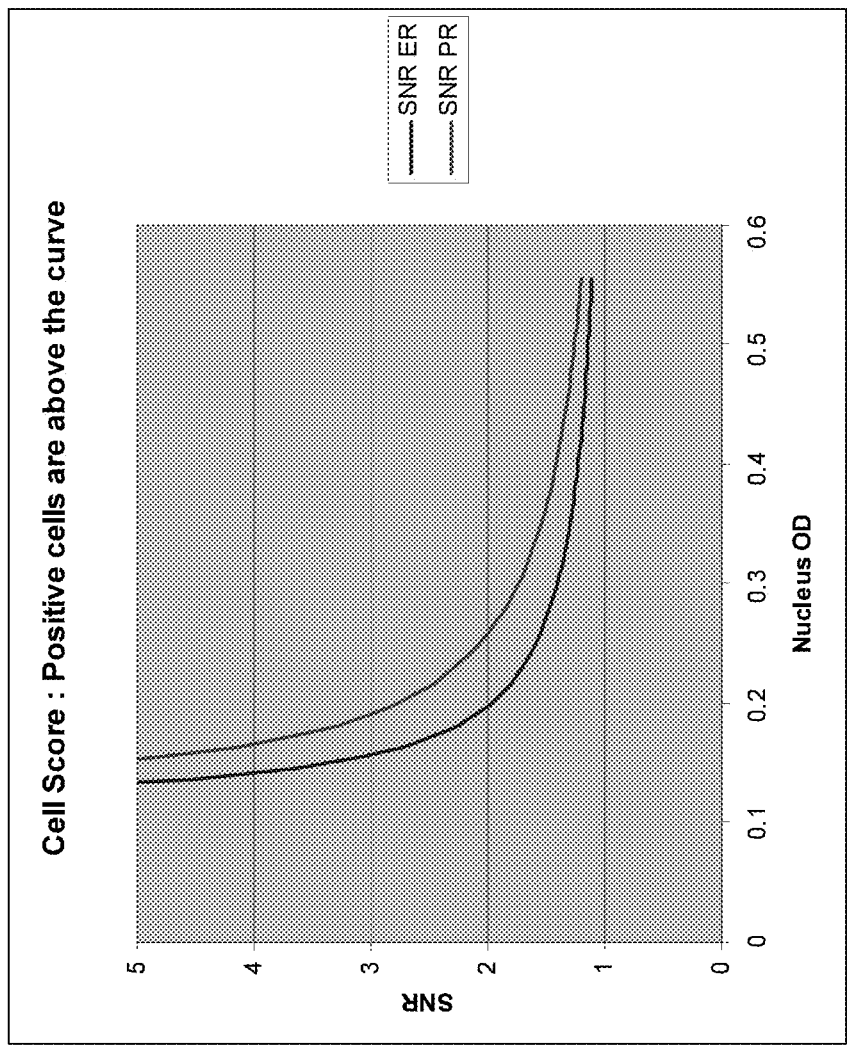

Accordingly, as shown in FIG. 4, any cell below the curve is negative, and positive otherwise. That is, FIG. 4 illustrates SNR and Nucleus OD curves defining, for ER and PR, the negative and positive status of a cell. For such nucleus markers, the Signal to Noise Ratio (SNR) is evaluated as a ratio of the Nucleus OD to the Cytoplasmic marker OD. If a cell falls above the curve (upper right corner) the cell is considered positive, and negative otherwise. Generally, the stronger the nucleus intensity, the less the SNR must be in order to call the cell positive (and vice-versa).

3b) Overall Score

An overall score can be attributed to a case that reflects, for that case, the information requested by the pathologist to establish his diagnosis/prognosis.

$$\text{Overall score} = 100 * \text{\# positive cells/\# cells in } ROI \quad (30)$$

In case of the ER and/or PR tests, the overall score requested by the pathologist is the percentage of positive cells within the tumor region. Therefore, once the pathologist is confident in his diagnosis/prognosis of the proposed region of interest (automatically proposed or manually drawn), the percentage of positively-scored cells is reported.

Integration Concept

Figure 5A:
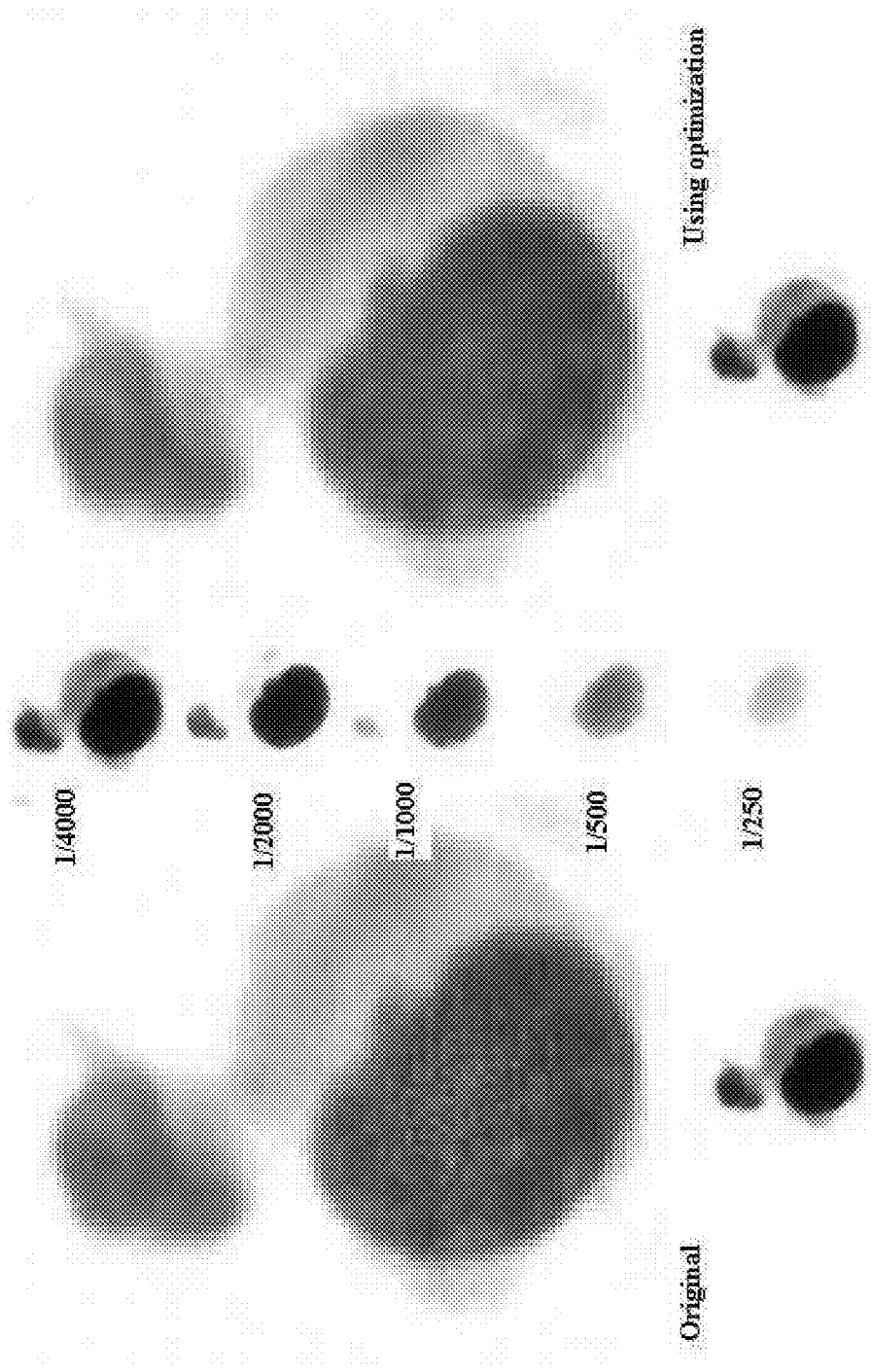

To further investigate the OD contribution of the different dyes when concentrations are very high and bit-wise limitations of the camera are reached, a strategy based upon time integration (shutter speed) of the camera can be implemented. That is, the same field of view is imaged with the same camera, but with different integration times. As shown in FIGS. 5A and 5B, the measured OD is normalized with the integration time and measured non-saturated values corresponding to the maximum integration time in each channel are retained. More particularly, FIG. 5A shows a particular cell with high marker intensity that is image-captured using different integration times (4000 $s^{-1}$ to 250 $s^{-1}$) to improve bit resolution in the darkest regions. According to such a methodology, pixelation of the chromogen-separated image in the nucleus (hematoxylin only) substantially disappears when the appropriate bit resolution is used. FIG. 5B shows RGB transmitted light intensities, as well as time-normalized OD values for one representative pixel captured using different integration times (4000 $s^{-1}$ to 250 $s^{-1}$) to improve bit resolution in the darkest regions of the image shown in FIG. 5A. The bit resolution improvement is derived from RGB transmitted light intensity values that are selected in each of the RGB channels for the integration time prior to saturation.

Breaking the 3D Limit Using RGB Input: 4D Chromogen Separation

One example of such a procedure for 4D chromogen separation is provided by a combination of 4 dyes for a modified PAP procedure, as shown in FIGS. 6A-6B, namely Hematoxylin (FIG. 6A), Eosin (FIG. 6B), Green (FIG. 6C), and DAB (FIG. 6D). In this instance, 3 channels (R, G, and B) comprise the input channels, with 4 unknowns (dyes). In such an instance, a priori knowledge can be used. The dyes are represented in a Maxwell equivalent plane which includes the extinction coefficient plane where EcR+EcG+EcB=1. In this plane, a dye is represented by a unique XY location. In each XY location of the plane, different RGB triplets showing different transmittances (different intensities of a given dye) can be presented, wherein, in the present example, an RGB triplet having the closest to 50% transmittance is shown in FIG. 7A. More particularly, FIG. 7A shows different RGB triplets, such as the RGB triplet closest to 50% transmittance. Each dye is projected on the Ec plane based upon its extinction coefficients in the red, green and blue channels of the image capturing device (camera), with each dye being represented by its initial letter.

With respect to the nature of the respective dyes, there are two accepted 3 dye configurations among the 4 possible configurations of the 3 dyes, as shown in FIGS. 7B1 and 7B2, respectively, wherein these two 3 dye configurations are each highlighted by a surrounding triangle. From a priori knowledge, it is known to be unlikely that all 4 dyes will be significantly present at the same geographical location with respect the sample. Therefore, chromogen separation in this instance considers only 3 dyes configurations where the 3 dyes could be co-located with respect to the sample. More particularly, Eosin and Green are mainly cytoplasmic dyes which stain cells with different cytoplasmic attributes. Consequently, these dyes are not likely to be present at the same location with respect to the sample even though, due to the location of the Hematoxylin between the Eosin and Green dyes in this extinction coefficient plane, a mixture of Eosin and Green could be mistaken with Hematoxylin (but is very unlikely to be mistaken for DAB).

Thus, in order to solve the 4D problem, the chromogen separation procedure is applied by looking for each RGB triplet of this FOV where, at the XY location thereof, the corresponding stain would be located, the XY location being the location in the extinction coefficient plane where EcR+EcG+EcB=1. In this plane, the surrounding 3D configuration, or by default the closest 3D configuration, is determined and used to solve the equations for optical density for the 3 corresponding dyes, while the remaining dye's optical density is set to 0. One skilled in the art will note that most of the XY locations of the investigated RGB triplets should lay within one of the 2 accepted 3 dye configurations. FIG. 8A illustrates a field of view having all 4 dyes represented (i.e., a typical modified PAP field of view where all 4 dyes are represented, wherein the dark central cell is DAB positive, as shown in FIG. 8C). FIGS. 8B-8E illustrate the same field for each of the 4 dyes.

Ultra-Fast Adaptation of the Scanner to Search for Positive (DAB) Cells in a Modified PAP Environment The discussed aspects of 4D chromogen separation and e-staining may, in some instances, combine to form another aspect of the present invention. More particularly, in continuation of the above example directed to the use of DAB and Hematoxylin, a scanner can be implemented that is capable of reading modified PAP slides (a DAB positive rare event solution), as shown in FIG. 9A (an RGB image of an original field of view). Then, based on the 4D chromogen separation and e-staining procedures, the 4 dye situation can be solved. Once solved, a simulated image can be reconstructed using an "e-staining" process to includes only the DAB and Hematoxylin contributions, as shown in FIG. 9B. In addition, the Hematoxylin and DAB only channels could be used as an input to the scanner, such that the scanner would be configured to capture a "Hematoxylin and DAB only" image, which would produce an image substantially the same as shown in FIG. 9B. Further, a simulated PAP-only image could be reconstructed using only the Hematoxylin, Eosin and Green contributions, as shown in FIG. 9C.

Taking RGB Distortion into Consideration

To accommodate and/or compensate for RGB distortion due to the image path, electronics, and/or staining variations, a modification of the chromogen separation can be considered. That is, imaging biological material stained with only one dye demonstrates that the extinction coefficient model, which can be calculated from each RGB triplet within the source FOV, varies slightly around the averaged accepted measure. Consequently when a dye mixture is present, multiple solutions of dye mixtures could be de facto accepted or acceptable. Different sources of noise could be responsible for such RGB distortion. For example, acquiring the image with a CMOS camera instead of a 3CCD camera could be one factor.

To compensate for these distortions, the dye-respective contribution solution for a given RGB triplet and a given multiple dye model is computed in a slightly different manner. More particularly, the RGB triplet under investigation is considered as the center of a ball in the RGB space having a given radius r. All triplets within this ball are investigated for their dye contribution solutions, and the solutions are averaged for each dye for all of the RGB triplets that satisfy the dye combination model. If no RGB triplet belongs to the dye combination model, the nearest RGB triplet within the ball to the dye combination model is retained as best potential candidate solution.

Dynamic Procedures

Traditionally, all algorithms or computational procedures used in quantitative microscopy applications are implemented or built into the system by software engineers. As such, each software release generally includes a limited set of algorithms, which cannot be changed without modification of the software ("software upgrades").

For example, an application may calculate the percent of positive cells on a slide by calculating the ratio of the number of cells having a mean optical density (MOD) of a marker stain in the cell nucleus greater than a threshold value to the total number of cells on the slide. In a traditional application, the threshold value may be configurable, but the formula used to calculate the ratio remains fixed; it will always compare the number of cells over a certain threshold to the total number of cells. Even if a procedure or algorithm allows the threshold value to vary based on other extracted features, the formulas used to determine the threshold are still fixed.

Accordingly, another aspect of the present invention comprises a methodology whereby the algorithms or procedures are configured to be dynamic (i.e., producing results based on formulas entered by a user). That is, instead of the algorithms or procedures being coded directly into the software, the software can evaluate the formulas to be used at actual analysis runtime. More particularly, a quantitative microscopy application implementing such dynamic algorithms first calculates or otherwise determines a general set of features at several levels, including a slide level, a TMA core level, a field level, and a cellular level. Such general features can then be aliased, thus defining different "variables" that may be combined in various forms with each other using, for example, standard mathematical operations, to form higher level features, or to define functions. As such, at analysis runtime, the application would load the list of aliased features and applicable formulas. When a formula is needed in the analysis, that formula is dynamically evaluated and the aliased features used to alter the formula as necessary. If a formula is frequently recalculated, or is sufficiently complex, such a formula or portion thereof may be precompiled to speed execution.

Such a method thus allows the set of algorithms or procedures implemented by the application to be updated, added to, or otherwise modified, in the field, without requiring any external modification to the software. As such, the application provides flexibility to the users, since new functionality can be created, as necessary and/or desired, without requiring any complex external software development. Such functions can, for example, generate numeric scores for the slides, cores, fields, or cells. In addition or in the alternative, such functions may provide a filtering capacity. As an example of the application of such functions, a user may define a function that calculates a percent positive, as described above, wherein the dynamic formulas may also be used to define a function that allows a display to highlight 'positive' cells, fields, or cores. Such dynamic formulas can also be used, for example, to define ranges for expected normal values, or named bins such as '0', '1+', '2+', etc.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of determining optical density data for at least one dye staining a sample from an image obtained with an imaging device, comprising:
    capturing a series of images of the sample at different integration times;
    selecting a highest non-saturated intensity in each of a red, green, and blue channel of the imaging device; and
    reconstructing an optimized image of the sample using the highest non-saturated intensity levels in the red, green, and blue channels such that the optimized image is suitable for chromogen separation.

2. A method according to claim 1 further comprising normalizing measured optical densities for each of the series of images in each of the red, green, and blue channels with respect to the corresponding integration time for the respective image, the highest non-saturated intensity being selected from the normalized measured optical densities.

* * * * *